(12) United States Patent
Banba et al.

(10) Patent No.: US 6,495,716 B2
(45) Date of Patent: Dec. 17, 2002

(54) [S,S]-ETHYLENEDIAMINE-N,N'-DISUCCINIC ACID CRYSTAL WITH HIGH BULK DENSITY AND PROCESS FOR OBTAINING THE SAME

(75) Inventors: Hiroyasu Banba, Yokohama (JP); Shigeho Tanaka, Yokohama (JP); Kiyonobu Niwa, Yokohama (JP); Takakazu Endo, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/083,536

(22) Filed: Feb. 27, 2002

(65) Prior Publication Data

US 2002/0082449 A1 Jun. 27, 2002

Related U.S. Application Data

(63) Continuation of application No. 09/530,964, filed as application No. PCT/JP98/05175 on Nov. 18, 1998.

(30) Foreign Application Priority Data

Nov. 18, 1997 (JP) ............................................. 9-332334

(51) Int. Cl.$^7$ .............................................. C07C 229/00
(52) U.S. Cl. ...................................... 562/562; 562/554
(58) Field of Search .................................. 562/565, 554

(56) References Cited

U.S. PATENT DOCUMENTS 5,587,512 A * 12/1996 Lin et al. ..................... 562/565

* cited by examiner

Primary Examiner—Paul J. Killos
Assistant Examiner—Taylor V. Oh
(74) Attorney, Agent, or Firm—Oblon, Spivak, McClelland, Maier & Neustadt, P.C.

(57) ABSTRACT

Crystals of [S,S]-ethylenediamine-N,N'-disuccinic acid which have a bulk density of 0.45 to 1.2 g/cm$^3$, and a process for obtaining these crystals comprising the steps of adjusting an aqueous solution of an [S,S]-ethylenediamine-N,N'-disuccinic acid metal salt to a temperature of 40 to 80° C. and a pH of 1.9 to 4.5, and cooling the solution to a temperature below 40° C. over a period of 0.2 to 10 hours while supplying a mineral acid so as to maintain the pH at 1.9 to 4.5 to precipitate [S,S]-ethylenediamine-N,N'-disuccinic acid in a high yield.

8 Claims, No Drawings

[S,S]-ETHYLENEDIAMINE-N,N'-DISUCCINIC ACID CRYSTAL WITH HIGH BULK DENSITY AND PROCESS FOR OBTAINING THE SAME

TECHNICAL FIELD

The present invention relates to [S,S]-ethylenediamine-N,N'-disuccinic acid crystals having a high bulk density and a process for obtaining the crystals in a high yield. [S,S]-ethylenediamine-N,N'-disuccinic acid (hereinafter abbreviated as [S,S]-EDDS) is expected to find use as a biodegradative chelating agent for a detergent composition, a photographic bleaching agent, an electroless plating assistant and a peroxide stabilizer, etc.

BACKGROUND ART

Several methods are known for a preparation of [S,S]-isomers of ethylenediamine-N,N'-disuccinic acid, such as (1) a chemical synthetic method in which said isomers are synthesized from L-aspartic acid and dibromoethane in a basic aqueous medium according to Neal and Rose et al. (Inorganic Chemistry, Vol. 7, pp. 2405–2412, 1968), (2) a chemical synthetic method in which the isomers are synthesized from L-aspartic acid and dibromoethane in the presence of calcium hydroxide according to Patel R. N. et al. (WO95-12570), (3) an enzymatic synthetic method in which the isomers are synthesized from fumaric acid and ethylenediamine according to Endo et al., and (4) a fermentative methods using actinomyces according to T. Nishikiori et al. (J. Antibiot. 37, 426–427, 1994) and Z. Hans et al. (WO9636725).

As methods for recovering [S,S]-EDDS, there have been proposed, for example, a method in which an [S,S]-EDDS solution is gradually made acidic with a concentrated hydrochloric acid till reaching the pH of 3.5 and then an objective substance is recovered from the solution according to Neal and Rose et al., a method for recovering from a clacium salt of [S,S]-EDDS (WO96-01801) according to Atkinson. Eldon. E. et al., and a method for recovering from an aqueous solution of [S,S]-EDDS and L-aspartic acid salt according to Atkinson. Eldon. E. et al. (WO96-01802). These proposals relate to techniques for recovering [S,S]-EDDS from an [S,S]-EDDS solution obtained by a chemical synthesis from L-aspartic acid and dibromoethane, and these techniques are intended to minimize an uptake of coprecipitates at the time of a recovery and to obtain a precipitate in such an amount that the precipitate can be easily filtered. Any of these proposals, however, are silent on how to obtain the crystals of [S,S]-EDDS with a high bulk density in a high yield.

According to experiments by the present inventors, the ordinary acid-precipitation method for example which comprises adding a mineral acid at a normal temperature or under cooling to a reaction liquid of [S,S]-EDDS obtained by the enzymatic synthetic method (3) as mentioned above involved problems that precipitated [S,S]-EDDS was extremely high bulky needle crystals, a deterging efficiency was bad, a drying efficiency of the produced crystals was bad, and a transportation efficiency of the crystals was poor because of their large volume per unit weight.

In order to solve the above problems, the present inventors have made extensive studies on crystallization conditions of [S,S]-EDDS such as a temperature, pH and a period of time at the time of the crystallization. In result, the present inventors found out the conditions under which columnar crystals having a high bulk density can be obtained, and quite unexpectedly confirmed that a considerable amount of cyclized products of ethylenediamine-N,N'-disuccinic acid represented by the following structural formulae (1) and (2) etc. were contained in a mother liquor in which formed crystals were removed, and that certain crystallization conditions promote an intramolecular cyclization reaction to cause a reduction of a recovery yield of [S,S]-EDDS.

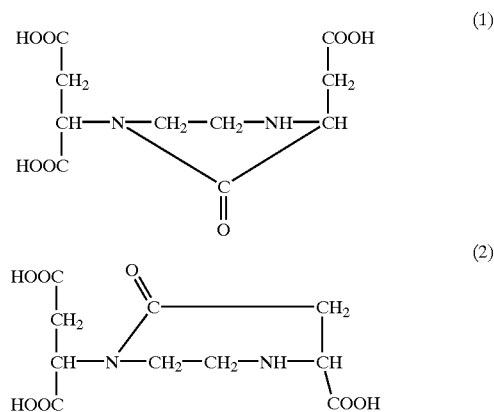

Accordingly, the purpose of the present invention is to suppress a formation of the cyclized products of [S,S]-EDDS at the time of crystallization and simultaneously to solve the various problems encountered in obtaining the [S,S]-EDDS crystals having a high bulk density. Solution of these problems is of vital importance for the industrial production of the crystals of [S,S]-EDDS.

Regarding cyclized products of ethylenediamine-N,N'-disuccinic acid, those derived from isomeric mixtures thereof ([R,R]-, [S,S]- and [R,S-/S,R]-mixtures) have been reported by Vasil' ev V.P. et al. (Zh. Neorg. Khim. 34(2), 381-385, 1989) and other researchers. However, there has been report neither on cyclized products derived from optically active [S,S]-isomers alone nor on a formation of the cyclized products at the time of crystallization.

DISCLOSURE OF THE INVENTION

As a result of intensive studies for a solution of the above problems, the present inventors found that it was effective for solving the above problems to conduct a crystallization under specified pH, temperature and period of time conditions, and succeeded in completing the present invention on the basis of this finding.

Thus, the present invention relates to: (1) crystals of [S,S]-ethylenediamine-N,N'-disuccinic acid having a bulk density of from 0.45 to 1.2 g/cm$^3$; (2) a process for obtaining the crystals described in (1), which comprises the steps of adjusting an aqueous solution of an [S,S]-ethylenediamine-N,N'-disuccinic acid metal salt to a temperature of from 40 to 80° C. and a pH of from 1.9 to 4.5 and then cooling the resulting solution to a temperature below 40° C. over a period of from 0.2 to 10 hours while supplying a mineral acid thereto so as to maintain the pH at from 1.9 to 4.5 to precipitate [S,S]-ethylenediamine-N,N'-disuccinic acid in a high yield; (3) the process for obtaining the crystals described in (1), which comprises the steps of supplying an aqueous solution of an [S,S]-ethylenediamine-N,N'-disuccinic acid metal salt and a mineral acid into an aqueous solution of an [S,S]-ethylenediamine-N,N'-disuccinic acid metal salt adjusted to a temperature of from 0 to 40° C. and a pH of from 1.9 to 4.5 so as to maintain the pH at from 1.9 to 4.5 and so as to make a residence time from 0.5 to 10 hours, and taking out intermittently or continuously the resulting slurry of [S,S]-ethylenediame-N,N'-disuccinic acid crystals in a high yield; (4) the process described in (2) or (3), wherein the yield of the crystal is 90% or more; (5) the process described in (4), in which a cyclization of [S,S]-ethylenediamine-N,N'-disuccinic acid during its crystallization is suppressed; (6) the process described in (2) or (3), wherein the [S,S]-ethylenediamine-N,N'-disuccinic acid metal salt is a sodium salt and/or a magnesium salt; and (7) the process described in (2) or (3), wherein the mineral acid is a sulfuric acid.

BEST MODE FOR CARRYING OUT THE INVENTION

[S,S]-EDDS contemplated in the present invention is the one having a composition that a ratio of [S,S]-isomers to a whole amount of isomers is 90% by weight or more.

The term "bulk density" referred to in the present invention is defined as a value determined according to JIS K5101 for a dry product with a water content (including crystal water) of 15% by weight or less.

The term "yield" referred to in the present invention is a value determined by dividing a weight obtained by subtracting a weight of [S,S]-ethylenediamine-N,N'-disuccinic acid disappearing at the time of crystallization from a weight of [S,S]-ethylenediamine-N,N'-disuccinic acid present in an aqueous solution of an ethylenediamine-N,N'-disuccinic acid salt, by a weight of [S,S]-ethylenediamine-N,N'-disuccinic acid present in the original aqueous solution, said value being expressed by percent.

Crystallization can be accomplished, for example, in the following way. In the case of a batch process, an aqueous solution of an alkaline metal salt, alkaline earth metal salt or ammonium salt etc. of [S,S]-EDDS with a concentration of from 0.1% by weight to a saturation concentration, obtained by the above-mentioned enzymatic synthetic method from fumaric acid and ethylenediamine (JP-A-9-140390 and EP-A-0805211), is adjusted to a pH in the range of 1.9 to 4.5, preferably 2.5 to 4.0, and a temperature in the range of 40 to 80° C., preferably 40 to 60° C., and, if necessary after causing a partial precipitation of [S,S]-EDDS or after adding seed crystals of [S,S]-EDDS, is gradually cooled. Cooling temperature is below 40° C., preferably 30 to 0° C., and cooling time, although variable depending on pH and temperature conditions, is in the range of from 0.2 to 10 hours. In the case of a continuous process, after adjusting the pH to the range of 1.9 to 4.5, preferably 2.4 to 4.0, and the temperature to the range of 0 to 40° C., an aqueous solution of an alkaline metal salt, alkaline earth metal salt or ammonium salt etc. of [S,S]-EDDS is supplied thereto so that a residence time become 0.5 to 10 hours, preferably 1 to 5 hours, although variable depending on pH and temperature conditions, and the resulting [S,S]-EDDS crystal slurry is taken out continuously or intermittently.

Although pH rises up gradually with proceeding of a crystallization, pH is adjusted so as to be in a prescribed range by adding an acid as required in this case.

Such pH adjustment can be usually made by adding a mineral acid such as sulfuric acid or hydrochloric acid.

On the other hand, the lower the pH or the higher the temperature or the longer the period of time of an exposure to these conditions, the easier formation of the cyclized products of ethylenediamine-N,N'-disuccinic acid represented by the structural formulae (1) and (2). The formation of the cyclized product not only causes a reduction of a recovery yield of the [S,S]-EDDS crystals but results in a cause of a reduction of a crystal quality because the cyclized product remaining in a mother liquor adheres to the crystals. However, the use of the above-mentioned preferable conditions can control a less formation of the cyclized product. According to the present invention, it is possible to finally obtain the [S,S]-EDDS crystals in a yield of 90% or more.

Ordinary methods such as filtration, centrifugation, etc., can be employed for collecting the the precipitated crystals. Then, the cyclized product and sulfates etc. formed in the acid-precipitation of crude crystals are washed away with water or an organic solvent. This washing is not subject to any specific restrictions, either, and ordinary washing methods such as rinsing and slurry washing etc. can be employed.

Drying of wet crystals after washing may be conducted at such a temperature that a temperature of the product be 80° C. or less.

The present invention is further illustrated by the following examples, but it should be understood that the present invention is not restricted by these examples in any way.

Methods of analyses and measurements made in the following Examples are as described below.
(1) [S,S]-EDDS and its Cyclized Product An [S,S]-EDDS solution or a 0.5N sodium hydroxide solution of crystals thereof centrifugally sterilized were analyzed by liquid chromatography (column: Inertsil ODS-3; mobile phase: 2 mM tetra-n-butylammonium hydroxide, 2 mM $CuSO_4$ and 50 mM $H_3PO_4$; flow rate: 1.0 ml/min; temperature: 40° C.; detecting wavelength: 220 nm).
(2) Optical Purity of Ethylenediamine-N,N'-disuccinic Acid An [S,S]-EDDS solution or a 0.5N sodium hydroxide solution of crystals thereof, in which cells had been centrifugally removed, were analyzed by liquid chromatography (column: MCl GEL CRS 10 W; mobile phase: 10 mM $CuSO_4$; flow rate: 0.5 ml/min; temperature: room temperature; detecting wavelength: 254 nm).
(3) Bulk Density Bulk density of dry crystals obtained was measured by a bulk density measuring instrument mfd. by Tokyo Kuramochi Kagaku Kikai Seisakusho Ltd. (JIS K5101).

Production Example 1

Preparation of [S,S]-EDDS Solution

Brevundimonas sp. TN-3 strain was cultured to obtain strain cells according to the method described in Example 1 of JP-A-9-140390. This TN-3 strain is described in EP-A-0805211, and it was deposited with National Institute of Bioscience and Human Technology, Agency of Industrial Science and Technology (1–3, Higashi 1-chome, Tsukubashi, Ibaraki-ken, Japan) on Apr. 11, 1996, and was afforded International Deposit No. FERM BP-5886 according to Budapest Treaty on the International Recognition of the Deposit of Microorganisms for the Purpose of Patent Procedure. The strain cells were suspended in a 100 mM boric acid buffer of pH 9.2 and heat-treated at 45° C. for 8 hours.

The treated strain cells were collected and then were suspended in a pH 8.5 reacting solution containing 143 g/l of fumaric acid, 37 g/l of ethylene-diamine and 54 g/l of magnesium hydroxide and reacted with stirring at 40° C. for 3 days while adjusting pH of the reaction mixture at 8.5 with a sodium hydroxide solution.

After the reaction was completed, the reaction product solution was centrifuged for removing the cells. The obtained supernatant contained 480 mM [S,S]-EDDS (a ratio of [S,S]-form to whole isomers being 98.8% by weight) and completely free of cyclized product of [S,S]-EDDS.

Comparative Example 1

Sulfuric acid was added to 100 ml of the above [S,S]-EDDS solution at room temperature (20° C.) to adjust its pH at 1.95. The solution was allowed to stand for one hour and precipitated crystals were filtered by a Buchner funnel and washed with 100 ml of desalted water to obtain wet crystals. Drying thereof overnight at 80°°C. gave needle crystals (0.05–0.2 mm in diameter and 0.5–3 mm length) with a bulk density of 0.2 g/cm$^3$ in a yield of 99.5%. Sulfate in the crystals was 264 ppm, and an amount of cyclized product in a mother liquor was about 0.5% based on [S,S]-EDDS supplied.

Comparative Example 2

To 100 ml of the above [S,S]-EDDS solution heated to 90° C., sulfuric acid was added to adjust its pH at 3.0. Then the solution was cooled gradually over a period of 2 hours until reaching 30° C., during which period sulfuric acid was gradually added to maintain pH at 3.0. Precipitated crystals were filtered by a Buchner funnel and washed with 100 ml of desalted water to obtain wet crystals. Drying thereof overnight at 80° C. gave columnar crystals (0.3–0.6 mm in diameter and 1–3 mm length) with a bulk density of 0.6 g/cm$^3$ in a yield of 80%. An amount of cyclized product in a mother liquor was about 20% based on [S,S]-EDDS supplied.

Comparative Example 3

To 100 ml of the above [S,S]-EDDS solution heated to 40° C., sulfuric acid was added to adjust the pH at 3.0, to which the above [S,S]-EDDS solution was further supplied at a rate of 1,000 ml/hr. In this operation, a slurry was taken out from time to time so as to maintain a liquid level at 100 ml (residence time: 0.1 hour). Also, during this period, sulfuric acid was gradually added to maintain the pH at 3.0. Precipitated crystals were filtered by a Buchner funnel and washed with 100 ml of desalted water to obtain wet crystals. Drying thereof overnight at 80° C. gave columnar crystals (0.1–0.2 mm in diameter and 0.3–1 mm length) with a bulk density of 0.3 g/cm$^3$ in a yield of 99.5%.

EXAMPLE 1

To 100 ml of the above [S,S]-EDDS solution heated to 80° C., sulfuric acid was added to adjust pH at 3.75. Then the solution was cooled gradually over a period of 2 hours until reaching 30° C., during which period sulfuric acid was gradually added so as to maintain pH at 3.75. Precipitated crystals were filtered by a Buchner funnel and washed with 100 ml of desalted water to obtain wet crystals. Drying thereof overnight at 80° C. gave columnar crystals (0.3–0.6 mm in diameter and 1–3 mm length) with a bulk density of 0.58 g/cm$^3$ in a yield of 91.5%. Sulfate in the crystals was 97 ppm, and an amount of cyclized product in a mother liquor was about 8.5% based on [S,S]-EDDS supplied.

EXAMPLE 2

To 100 ml of the above [S,S]-EDDS solution heated to 80° C., sulfuric acid was added to adjust pH at 3.2. Then, the solution was cooled to 60° C. over a period of 30 minutes, maintained at 60° C. for one hour and then again cooled gradually till reaching 21.5° C. over a period of one hour. During this period, sulfuric acid was gradually added to maintain the pH at 3.2. Precipitated crystals were filtered by a Buchner funnel and washed with 100 ml of desalted water to obtain wet crystals. Drying thereof overnight at 80° C. gave columnar crystals (0.3–0.6 mm in diameter and 1–3 mm length) with a bulk density of 0.57 g/cm$^3$ in a yield of 95.0%. Sulfate content in the crystals was 94 ppm, and an amount of cyclized product in a mother liquor was about 5% based on [S,S]-EDDS supplied.

EXAMPLE 3

To 100 ml of the above [S,S]-EDDS solution heated to 60° C., sulfuric acid was added to adjust pH at 3.2. The solution was maintained at 60° C. for 30 minutes and then cooled gradually until reaching 21.5° C. over a period of one hour. During this period, sulfuric acid was gradually added to maintain the pH at 3.2. Precipitated crystals were filtered by a Buchner funnel and was washed with 100 ml of desalted water to obtain wet crystals. Drying thereof overnight at 80° C. gave columnar crystals (0.3–0.6 mm in diameter and 1–3 mm length) with a bulk density of 0.55 g/cm$^3$ in a yield of 98.0%. Sulfate content in the crystals was 93 ppm, and an amount of cyclized product in a mother liquor was about 3% based on [S,S]-EDDS supplied.

EXAMPLE 4

To 100 ml of the above [S,S]-EDDS solution diluted to 3 times and heated to 40° C., sulfuric acid was added to adjust pH at 3.2. Then, the solution was maintained at 60° C. for 30 minutes and then cooled gradually till reaching 20° C. over a period of one hour. During this period, sulfuric acid was gradually added to maintain the pH at 3.2. Precipitated crystals were filtered by a Buchner funnel and washed with 100 ml of desalted water to obtain wet crystals. Drying thereof overnight at 80° C. gave columnar crystals (0.2–0.7 mm in diameter and 1–3.5 mm length) with a bulk density of 0.56 g/cm$^3$ in a yield of 99.5%. Sulfate content in the crystals was 90 ppm, and an amount of cyclized product in a mother liquor was about 0.5% based on [S,S]-EDDS supplied.

EXAMPLE 5

To 100 ml of the above [S,S]-EDDS solution heated to 40° C., sulfuric acid was added to adjust pH at 3.0, to which the above [S,S]-EDDS solution was further supplied at a rate of 50 ml/hr. In this operation, a slurry was taken out from time to time so as to keep a liquid level at 100 ml (residence time: 2 hours). During this period, sulfuric acid was gradually added to maintain the pH at 3.0. Precipitated crystals were filtered by a Buchner funnel and washed with 100 ml of desalted water to obtain wet crystals. Drying thereof overnight at 80° C. gave columnar crystals (0.3–0.7 mm in diameter and 0.5–1 mm length) with a bulk density of 0.61 g/cm$^3$ in a yield of 99%.

EXAMPLE 6

To 100 ml of the above [S,S]-EDDS solution heated to 20° C., sulfuric acid was added to adjust pH at 3.0, to which the above [S,S]-EDDS solution was further supplied at a rate of 30 ml/hr. In this operation, a slurry was taken out from time to time so as to keep a liquid level at 100 ml (residence time: 3.3 hours). During this period, sulfuric acid was gradually added to maintain the pH at 3.0. Precipitated crystals were filtered by a Buchner funnel and washed with 100 ml of desalted water to obtain wet crystals. Drying thereof overnight at 80° C. gave columnar crystals (0.3–0.6 mm in diameter and 0.4–1 mm length) with a bulk density of 0.58 g/cm$^3$ in a yield of 99.5%.

Industrial Applicability

Crystals of [S,S]-EDDS according to the present invention are columnar crystals (about 0.3–0.7 mm in diameter and about 0.5–1 mm length) with a bulk density of 0.45 to 1.2 g/cm$^3$. These crystals are far better in washing, drying and transporting efficiencies than needle crystals (about 0.05–0.2 mm in diameter and about 0.5–3 mm length) with a bulk density of about 0.2 g/cm$^3$ obtained by the conventional acid-precipitation method in which a mineral acid is added at normal temperature or under cooling. Also, the [S,S]-EDDS crystals of the present invention are substantially free of impurities such as salts and cyclized product of [S,S]-EDDS formed during acid precipitation, hence are high in quality. Further, these crystals can be obtained in a high yield.

What is claimed is:

1. Crystal of (S,S)-ethylenediamine-N,N'-disuccinic acid, which are columnar crystals having a bulk density of from 0.45 to 1.2 g/cm$^3$.

2. The crystals of claim 1, which are about 0.3–0.7 mm in diameter and about 0.5–1 mm in length.

3. The crystals of claim 1 which are substantially free of impurities formed by cyclization of (S,S)-ethylenediamine-N,N'-disuccinic acid during acid precipitation.

4. The crystals of claim 1, having a bulk density of from 0.55 to 0.61 g/cm$^3$.

5. The crystals of claim 1, having a bulk density of 0.58 g/cm$^3$.

6. The crystals of claim 1, having a bulk density of 0.57 g/cm$^3$.

7. The crystals of claim 1 having a bulk density of 0.55 g/cm$^3$.

8. The crystals of claim 1, having a bulk density of 0.56 g/cm$^3$.

* * * * *